(12) United States Patent
Mole

(10) Patent No.: US 8,549,994 B2
(45) Date of Patent: Oct. 8, 2013

(54) PRODUCE DECONTAMINATION APPARATUS

(75) Inventor: Alan Mole, Pershore (GB)

(73) Assignee: Steritrox Limited, Cheshire (GB)

( * ) Notice: Subject to any disclaimer, the term of this patent is extended or adjusted under 35 U.S.C. 154(b) by 1042 days.

(21) Appl. No.: 10/578,605

(22) PCT Filed: Nov. 4, 2004

(86) PCT No.: PCT/GB2004/004636
§ 371 (c)(1),
(2), (4) Date: Mar. 26, 2007

(87) PCT Pub. No.: WO2005/046741
PCT Pub. Date: May 26, 2005

(65) Prior Publication Data
US 2007/0261570 A1  Nov. 15, 2007

(30) Foreign Application Priority Data

Nov. 5, 2003 (GB) .................................. 0325775.5
Jul. 20, 2004 (GB) .................................. 0416146.9

(51) Int. Cl.
*A01J 11/04* (2006.01)
*A01J 13/00* (2006.01)
*A01J 15/14* (2006.01)
*A61L 2/00* (2006.01)
*A61L 2/18* (2006.01)
*A61L 9/00* (2006.01)
*B01J 19/08* (2006.01)
*B01J 19/12* (2006.01)

(52) U.S. Cl.
USPC ........... 99/467; 422/28; 422/186.07; 422/292

(58) Field of Classification Search
USPC .................. 99/467, 453, 477, 478, 516, 534, 99/644; 426/335, 248, 615; 422/28, 32, 422/186.07, 186.08, 292, 300, 302, 304
See application file for complete search history.

(56) References Cited

U.S. PATENT DOCUMENTS 1,719,631 A * 7/1929 Stott .............................. 99/517
2,316,159 A * 4/1943 James ........................... 134/63
(Continued)

FOREIGN PATENT DOCUMENTS

DE  200 15 853 U1  10/2001
DE  20015853 U1 * 10/2001
(Continued)

OTHER PUBLICATIONS

L. E. Eary, Catalytic decomposition of hydrogen peroxide by ferric ion in dilute sulfuric acid, Jun., 1985, Springer Boston, vol. 16, No. 2, p. 181.*

(Continued)

*Primary Examiner* — Henry Yuen
*Assistant Examiner* — Hemant Mathew
(74) *Attorney, Agent, or Firm* — Fleit Gibbons Gutman Bongini & Bianco PL; Martin Fleit; Paul D. Bianco

(57) ABSTRACT

The invention provides a produce decontamination apparatus comprising a chamber 10 for accepting produce to be decontaminated and/or sterilized, and means for producing a free radical saturated atmosphere within the chamber 10 so that, in use, the free radical saturated atmosphere decontaminates and/or sterilizes the produce. Preferably, the means for producing a free radical saturated atmosphere comprises one or more first atomizing sprayheads 30a, a supply 32 of ozonized liquid which is supplied to the first sprayheads 30a, and means for breaking down the ozone forming part of the ozonized liquid once discharged from the first sprayheads 30a. Preferably, the means for breaking down the ozone is in the form of one or more UV light emitting devices 48,50. Produce decontaminated using the apparatus is also provided.

16 Claims, 1 Drawing Sheet

(56) References Cited

U.S. PATENT DOCUMENTS

| | | | | |
|---|---|---|---|---|
| 2,417,932 | A * | 3/1947 | Kalmar | 426/253 |
| 2,504,946 | A * | 4/1950 | Doolittle | 209/45 |
| 4,331,691 | A * | 5/1982 | Poovaiah et al. | 426/302 |
| 4,800,090 | A * | 1/1989 | August | 426/243 |
| 5,405,631 | A * | 4/1995 | Rosenthal | 426/235 |
| 5,458,051 | A * | 10/1995 | Alden et al. | 99/349 |
| 5,858,435 | A * | 1/1999 | Gallo | 426/320 |
| 6,725,674 | B1 * | 4/2004 | Kamm et al. | 62/63 |
| 6,821,353 | B1 * | 11/2004 | Kuhl | 134/6 |
| 6,964,788 | B2 * | 11/2005 | Phebus et al. | 426/335 |
| 2003/0068447 | A1 * | 4/2003 | Carling | 427/535 |
| 2003/0133832 | A1 * | 7/2003 | D'Ottone | 422/29 |
| 2004/0120845 | A1 * | 6/2004 | Potember et al. | 422/4 |
| 2005/0089458 | A1 | 4/2005 | Oke | |

FOREIGN PATENT DOCUMENTS

| | | | |
|---|---|---|---|
| EP | 529937 | A2 * | 3/1993 |
| EP | 0 722 741 | A | 7/1996 |
| EP | 722741 | A2 * | 7/1996 |
| WO | WO 01/78793 | A | 10/2001 |
| WO | WO 0178793 | A1 * | 10/2001 |
| WO | WO 02/05665 | A1 | 1/2002 |
| WO | WO 0205665 | A1 * | 1/2002 |
| WO | WO 03/038351 | A | 5/2003 |
| WO | WO 03038351 | A1 * | 5/2003 |
| WO | WO 2004/060817 | A1 | 7/2004 |
| WO | WO 2004060817 | A1 * | 7/2004 |

OTHER PUBLICATIONS

Singh, N; Pisarczyk, KS; Sigmund, JJ, Catalytic destruction of ozone at room temperature, Air & Waste Management Association, 1997.*
International Search Report published Sep. 15, 2005 for PCT/GB2004/004636 filed Nov. 4, 2004.
International Preliminary Report on Patentability published May 8, 2005 for PCT/GB2004/004636 filed Nov. 4, 2004.
Written Opinion of the International Searching Authority published May 5, 2005 for PCT/GB2004/004636 filed Nov. 4, 2004.
British Search Report for application No. GB0416146.9 filed Jul. 20, 2004. Date of search Nov. 23, 2004.

* cited by examiner

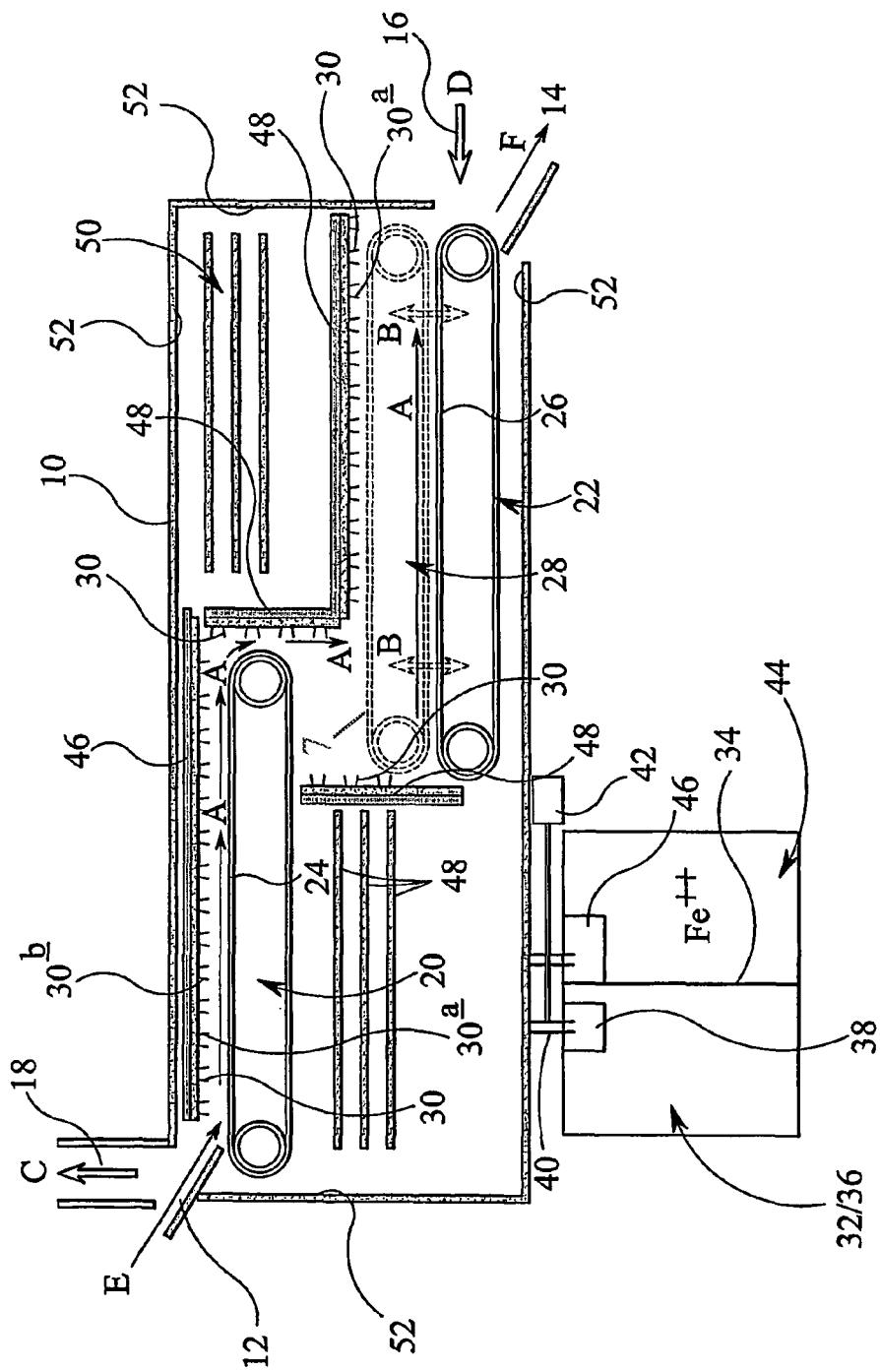

PRODUCE DECONTAMINATION APPARATUS

CROSS-REFERENCE TO RELATED APPLICATION

This application is a U.S. national stage of PCT International Application No. PCT/GB2004/004636, filed on Nov. 4, 2004.

FIELD OF THE INVENTION

This invention relates to produce decontamination apparatus and, more particularly, to the decontamination of produce by free radical washing.

BACKGROUND OF THE INVENTION

Fresh produce is typically washed, post harvest, with various decontaminating solutions containing biocide, such as chlorine/chlorine dioxide, ozone, or any number of combinations of chemicals. This is intended to reduce the risk of introducing potentially damaging or pathogenic microorganisms to the consumer.

However, the use of chemicals within the food chain is now less acceptable, and many chemical biocides are now limited by legislation.

Traditional techniques of sanitisation or decontamination use vast quantities of water, which is also a valuable commodity.

The present invention seeks to provide a solution to these problems.

BRIEF SUMMARY OF THE INVENTION

According to a first aspect of the present invention, there is provided produce decontamination apparatus comprising a chamber for accepting produce to be decontaminated and/or sterilised, and means for producing a free radical saturated atmosphere within the chamber so that, in use, the free radical saturated atmosphere decontaminates and/or sterilises the produce.

Preferable and/or optional features of the invention are set forth in the claims.

According to a second aspect of the present invention, there is provided produce decontaminated using produce decontamination apparatus in accordance with the first aspect of the invention.

BRIEF DESCRIPTION OF THE FIGURES

The invention will now be more particularly described, by way of example only, with reference to the only accompanying FIGURE.

FIG. 1 shows diagrammatically a cross-sectional elevation view of one embodiment of the produce decontamination apparatus.

DETAILED DESCRIPTION OF THE INVENTION

Referring to FIG. 1, there is shown produce decontamination apparatus which comprises a substantially enclosed chamber 10 which is open to atmospheric pressure and which has a produce inlet 12, a produce outlet 14, an air inlet 16, a pumped chamber exhaust 18, and two conveyors 20 and 22. Each conveyor 20 and 22 includes a conveyor belt 24 and 26 fully housed within the chamber 10. The conveyor belts 24 and 26 are vertically spaced apart and horizontally positioned relative to each other so that one end of the upper conveyor belt 24 overhangs the lower conveyor belt 26. A produce flow path is thus generated horizontally along the upper conveyor belt 24, vertically down from the upper conveyor belt 24 to the lower conveyor belt 26, and then horizontally along the lower conveyor belt 26, as indicated by arrows A.

The vertical spacing between the upper and lower conveyor belts 24 and 26 is adjustable through an adjustment mechanism (not shown). The adjustment mechanism typically allows height adjustment of the lower conveyor belt 26, as shown in the FIGURE by the phantom lines 7 and arrows B. However, the upper conveyor belt 24 could alternatively or additionally be height adjustable. An adjusted position 28 is shown in the figure.

Sprayheads 30 are located within the chamber 10, and form part of means for producing a free radical saturated atmosphere. The sprayheads 30 are provided along the full extent of the produce flow path A. More specifically, the sprayheads 30 are provided at a constant spacing directly above each conveyor belt 24 and 26 and also at the vertical spacing between the upper and lower conveyor belts 24 and 26. Since the vertical spacing between the upper and lower conveyor belts 24 and 26 is an open space, the sprayheads 30 are provided on at least two sides.

The sprayheads 30 are atomising sprayheads and discharge a non-condensing mist of liquid having a droplet size of between 1 and 15 microns. The average droplet size is preferably 5 microns.

The sprayheads 30 are divided into ozone and ferrous sprayheads 30a and 30b. The ozone sprayheads 30a are fluidly-connected to a first supply 32 of ozonised liquid, typically being ozonised water; and the ferrous sprayheads 30b are fluidly-connected to a second supply 34 of liquid, typically water, having ferrous ions. The first and second supplies 32 and 34 reside externally of the chamber 10.

The first supply 32 includes a reservoir 36 and a pump 38 for supplying the liquid in the reservoir 36 to the ozone sprayheads 30a at the correct pressure to ensure atomisation. The liquid passing from reservoir 36 to the ozone sprayheads 30a is initially pumped through a venturi 40 or any other similar device by which ozone from an ozone generator 42 can be introduced. The ozone concentration is regulated at between 1 and 5 parts-per-million (ppm).

The second supply 34 includes a reservoir 44 and a pump 46. The liquid in the reservoir 44 is charged with ferrous salts, such as ferrous Sulphate, typically in the concentration of 10 to 15 ppm. However, different concentrations depending on necessity can be used.

The ferrous sprayheads 30b and the second supply 34 together form means for catalysing the breakdown of hydrogen peroxide which is formed by the breakdown of ozone discharged as part of the ozonised liquid from the ozone sprayheads 30a.

The ozone and ferrous sprayheads 30a and 30b are provided in alternating fashion along the produce flow path A. A ferrous sprayhead 30b is provided at the beginning of the flow path A.

Means for breaking down the ozone discharged as part of the ozonised liquid from the first sprayheads 30a are in the form of ultraviolet light emitting devices 48, typically being UV fluorescent tubes. The UV light emitting devices 48 are waterproof and are mounted along the full extent of the produce flow path. Specifically, the UV light emitting devices 48 are positioned at a constant spacing directly above the upper and lower conveyor belts 24 and 26, and at the vertical spacing between the two conveyor belts 24 and 26. As with the sprayheads 30, the UV light emitting devices 48 are positioned on at least two sides at the vertical spacing between the two conveyor belts 24 and 26.

Further UV light emitting devices 50 are also provided in any redundant spaces within the chamber 10 to ensure full exposure of the ozonised liquid to the ultraviolet light.

The UV light emitting devices 48,50 emit ultraviolet light at wavelengths of between 185 and 253.7 nanometers.

To catalyse the breakdown of the ozone discharged as part of the ozonised liquid from the ozone sprayheads 30a, the interior surfaces 52 of the chamber 10 have a coating including an ozone catalysing agent or agents. At least one of the ozone catalysing agents is titanium oxide or titanium dioxide. This coating forms ozone catalysing means, and helps to ensure that there is no build up of ozone contamination within the chamber 10.

Ozone in solution breaks down rapidly when subjected to ultraviolet light to form hydrogen peroxide $H_2O_2$, which itself then breaks down to form peroxide radicals HO—OH, and finally highly reactive hydroxyl radicals OH. and $OH^-$. The rate of conversion from hydrogen peroxide to hydroxyl radicals can be greatly enhanced by the use of ferrous ions $Fe^{2+}$, which act as a catalyst during their conversion to ferric ions $Fe^{3+}$. This is generally known as Fenton's Reaction, and follows the formula:

$$H_2O_2 + Fe^{2+} = OH. + OH^- + Fe^{3+}$$

In use, a dense mist is generated in the interior of the chamber 10 through discharge of atomised ozonised liquid via the ozone sprayheads 30a and atomised liquid having ferrous ions via the ferrous sprayheads 30b. The atmosphere within the interior of the chamber 10 thus becomes saturated with free radicals resulting from the catalysed breakdown of the ozone of the discharged ozonised liquid and the hydrogen peroxide.

To ensure that the free radical saturated atmosphere does not leak out to the general environment in which the apparatus is placed, the pumped chamber exhaust 18 generates a slight negative pressure within the chamber 10 by recirculating a portion of the free radical saturated atmosphere (arrow C) and promoting the ingress of ambient air through air inlet 16 (arrow D).

Produce to be decontaminated or sterilised is introduced into the chamber 10 through produce inlet 12 (arrow E). The produce is first subjected to a spray of the liquid having the ferrous ions from the ferrous sprayhead 30b at the beginning of the flow path A. This initially coats the surface of the produce with liquid having ferrous ions. The produce is then exposed to the ozonised liquid from the next ozone sprayhead 30a. This ensures that free radical generation is strongest on the surface of the produce.

The produce travels on the upper conveyor belt 24 and moves along the rest of the flow path A through the dense free radical saturated atmosphere within the chamber 10. Depending on the produce and the length of time needed for sufficient decontamination, the speed of the conveyor belts 24 and 26 can be adjusted.

The produce drops through the vertical spacing between the upper and lower conveyor belts 24 and 26. This enables the entire exterior surface of the produce to be fully exposed to the free radical atmosphere as it passes through the vertical spacing, and also the positioning of the produce to be altered from one conveyor belt 24 to the conveyor belt 26, thereby allowing other surfaces of the produce to be exposed to the free radical atmosphere for an extended period.

Again, depending on the produce, the distance of the vertical spacing between the upper and lower conveyor belts 24 and 26 will be pre-adjusted to prevent damage to the produce.

On reaching the end of the flow path A, the produce exits the chamber 10 through the produce outlet 14 (arrow F) and is collected by any suitable means.

By the generation and use of free radicals, a powerful oxidising agent and biocide can be utilised to decontaminate produce. This can be enhanced by the use of Fenton's Reaction and the incorporation of a second liquid having ferrous ions.

The volume of liquid necessary to produce the dense free radical saturated atmosphere within the chamber is nominal, and is preferably two to four liters per hour per sprayhead. By way of example, a chamber having twenty sprayheads therefore uses no more than eighty liters of water per hour. Such a chamber has a produce decontamination capacity of several hundred kilograms per hour.

It is thus possible to provide apparatus which can decontaminate or sterilise produce without the need for submersion in a chemically treated liquid. It is also possible to provide apparatus which dramatically reduces the amount of liquid required for decontaminating produce.

The embodiment described above is given by way of example only, and modifications will be apparent to persons skilled in the art without departing from the scope of the invention as defined by the appended claims.

The invention claimed is:

1. A produce decontamination apparatus comprising a substantially enclosed chamber for accepting produce to be decontaminated and/or sterilised, the chamber having a negative pressure and including a produce inlet and a produce outlet, means for producing a free radical saturated atmosphere within the chamber so that, in use, the free radical saturated atmosphere decontaminates and/or sterilises the produce, the means for producing a free radical saturated atmosphere including one or more first atomising sprayheads, a supply of ozonised liquid which is supplied to the first sprayheads, means for breaking down an ozone forming part of the ozonised liquid once discharged from the first sprayheads, and means for catalysing breakdown of hydrogen peroxide formed from ozone of the ozonised liquid once the ozonised liquid is discharged from the first spray heads, the chamber including at least two conveyor belts that are vertically spaced apart and horizontally positioned relative to each other so that one end of an upper conveyor belt overhangs a lower conveyor belt whereby produce is moved along the upper conveyor belt and dropped to the lower conveyor belt to be fully exposed to the free radical saturated atmosphere prior to exit from the chamber wherein the means for catalysing the breakdown of hydrogen peroxide includes one or more second atomising sprayheads, and a supply of catalysing liquid which is supplied to the second sprayheads, the catalysing liquid catalysing the breakdown of the hydrogen peroxide formed from the ozone of the ozonised liquid once the catalysing liquid is discharged from the second sprayheads.

2. The apparatus as claimed in claim 1, wherein the means for breaking down the ozone forming part of the ozonised liquid is an ultraviolet emitting device.

3. The apparatus as claimed in claim 1, wherein the catalysing liquid includes ferrous ions.

4. The apparatus as claimed in claim 1, wherein vertical spacing between the upper conveyor belt and the lower conveyor belt is adjustable.

5. The apparatus as claimed in claim 1, wherein the chamber is open to atmospheric pressure.

6. The apparatus as claimed in claim 1, wherein said means for breaking down the ozone forming part of the ozonised liquid include a coating on an interior of the chamber, the coating having one or more ozone catalysing materials.

7. The apparatus as claimed in claim 6, wherein at least one of the ozone catalysing materials is titanium oxide, titanium dioxide, or manganese oxide.

8. A produce decontamination apparatus comprising:
   a) a substantially enclosed chamber for accepting produce to be decontaminated and/or sterilized, the chamber having a negative pressure and including a produce inlet and a produce outlet;
   b) means for producing a free radical saturated atmosphere within the chamber so that, in use, the free radical saturated atmosphere decontaminates and/or sterilizes the produce, the means for producing a free radical saturated atmosphere including one or more first atomizing sprayheads provided along a length of a produce flow path through the chamber and a supply of ozonized liquid which is supplied to the one or more first atomizing sprayheads;
   c) means for breaking down an ozone forming part of the ozonized liquid once the ozonized liquid is discharged from the one or more first atomizing sprayheads, the means for breaking down an ozone forming part of the ozonized liquid including an ultraviolet emitting device;
   d) means for breaking down hydrogen peroxide formed from reaction of the ozone forming part of the ozonized liquid and ultraviolet light emitting from the ultraviolet light emitting device; the means for breaking down hydrogen peroxide formed from reaction of the ozone forming part of the ozonized liquid including one or more second atomizing sprayheads provided along the length of the produce flow path and a supply of catalyzing liquid for catalyzing breakdown of hydrogen peroxide which is supplied to the one or more second atomizing sprayheads; and
   e) at least two conveyor belts provided within the chamber to create the produce flow path; the conveyor belts vertically spaced and horizontally positioned relative to each other creating an upper conveyor belt and a lower conveyor belt and arranged such that one end of the upper conveyor belt overhangs the lower conveyor belt whereby produce is moved along the upper conveyor belt and dropped to the lower conveyor belt to be fully exposed to the free radical saturated atmosphere prior to exit from the chamber.

9. The apparatus as claimed in claim 8, wherein the one or more first sprayheads and the one or more second sprayheads are provided in a constant spacing directly above horizontal lengths of the upper conveyor belt and the lower conveyor belt and are provided on at least two sides of the conveyor belts in a vertical space between the upper and lower conveyor belt.

10. The apparatus as claimed in claim 8, wherein the catalyzing liquid includes ferrous ions.

11. The apparatus as claimed in claim 8, wherein vertical spacing between the upper conveyor belt and the lower conveyor belt is adjustable.

12. The apparatus as claimed in claim 8, wherein the chamber is open to atmospheric pressure.

13. The apparatus as claimed in claim 8, wherein said means for breaking down the ozone forming part of the ozonized liquid further include a coating on an interior of the chamber, the coating having one or more ozone catalyzing materials.

14. The apparatus as claimed in claim 13, wherein at least one of the ozone catalyzing materials is titanium oxide, titanium dioxide, and manganese oxide.

15. A produce decontamination apparatus comprising:
   a) a substantially enclosed chamber for accepting produce to be decontaminated and/or sterilized, the chamber having a negative pressure and including a produce inlet and a produce outlet;
   b) at least two conveyor belts provided within the chamber to create a produce flow path; the conveyor belts vertically spaced and horizontally positioned relative to each other creating an upper conveyor belt and a lower conveyor belt;
   c) means for producing a free radical saturated atmosphere within the chamber so that, in use, the free radical saturated atmosphere decontaminates and/or sterilizes the produce, the means for producing a free radical saturated atmosphere including:
      i) one or more first atomizing sprayheads provided along a length of the produce flow path through the chamber, the one or more first atomizing sprayheads provided in a constant spacing directly above horizontal lengths of the upper conveyor belt and the lower conveyor belt and provided on at least two sides of the conveyor belts and in a vertical space between the upper conveyor belt and the lower conveyor belt; and
      ii) a supply of ozonized liquid which is supplied to the one or more first atomizing sprayheads;
   d) means for breaking down an ozone forming part of the ozonized liquid once the ozonized liquid is discharged from the one or more first atomizing sprayheads, the means for breaking down an ozone forming part of the ozonized liquid including an ultraviolet emitting device;
   e) means for breaking down hydrogen peroxide formed from reaction of the ozone forming part of the ozonized liquid and ultraviolet light emitting from the ultraviolet light emitting device; the means for breaking down hydrogen peroxide formed from reaction of the ozone forming part of the ozonized liquid including:
   i) one or more second atomizing sprayheads provided along a length of the produce flow path through the chamber, the one or more second atomizing sprayheads provided in a constant spacing directly above horizontal lengths of the upper conveyor belt and the lower conveyor belt and provided on at least two sides of the conveyor belts and in a vertical space between the upper conveyor belt and the lower conveyor belt; and
   ii) a supply of catalyzing liquid which is supplied to the one or more second atomizing sprayheads; wherein the upper conveyor belt and the lower conveyor belt are arranged such that one end of the upper conveyor belt overhangs the lower conveyor belt whereby produce is moved along the upper conveyor belt and dropped to the lower conveyor belt to be fully exposed to the free radical saturated atmosphere prior to exit from the chamber.

16. The apparatus as claimed in claim 15, wherein the catalyzing liquid includes ferrous ions.

* * * * *

UNITED STATES PATENT AND TRADEMARK OFFICE
CERTIFICATE OF CORRECTION

PATENT NO. : 8,549,994 B2  Page 1 of 1
APPLICATION NO. : 10/578605
DATED : October 8, 2013
INVENTOR(S) : Alan Mole It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1408 days.

Signed and Sealed this
Fifteenth Day of September, 2015

Michelle K. Lee
*Director of the United States Patent and Trademark Office*